United States Patent [19]
Dewey, Jr.

[11] 3,950,101
[45] Apr. 13, 1976

[54] MEASURING THE HEATING VALUE OF A FUEL IN THE GASEOUS STATE: METHOD AND APPARATUS

[75] Inventor: C. Forbes Dewey, Jr., Belmont, Mass.

[73] Assignee: Thermo Electron Corporation, Waltham, Mass.

[22] Filed: Feb. 1, 1974

[21] Appl. No.: 438,902

[52] U.S. Cl. ............... 356/51; 250/341; 250/345; 356/93; 356/189; 356/201
[51] Int. Cl.² ........................................ G01N 21/24
[58] Field of Search ................................. 73/190 R; 250/339–341, 343–345; 356/51, 93–97, 74, 179, 88, 186, 188, 189, 201, 204–206

[56] References Cited
UNITED STATES PATENTS

| | | | |
|---|---|---|---|
| 2,170,435 | 8/1939 | Sweeney | 356/51 |
| 2,765,409 | 10/1956 | Hutchins et al. | 250/343 |
| 2,813,010 | 11/1957 | Hutchins | 250/345 |

*Primary Examiner*—John K. Corbin
*Assistant Examiner*—F. L. Evans
*Attorney, Agent, or Firm*—James L. Neal

[57] ABSTRACT

A spectrophotometric method is disclosed for measuring the heating value of a mixture of substances commonly comprising a gaseous fuel. The method is based on the recognition that within certain wavebands the mixture exhibits a correlation between heating value and the strength of radiant energy absorption. A spectrophotometric apparatus is disclosed which is adapted to permit the continuous observation of the heating value of the mixture.

11 Claims, 11 Drawing Figures

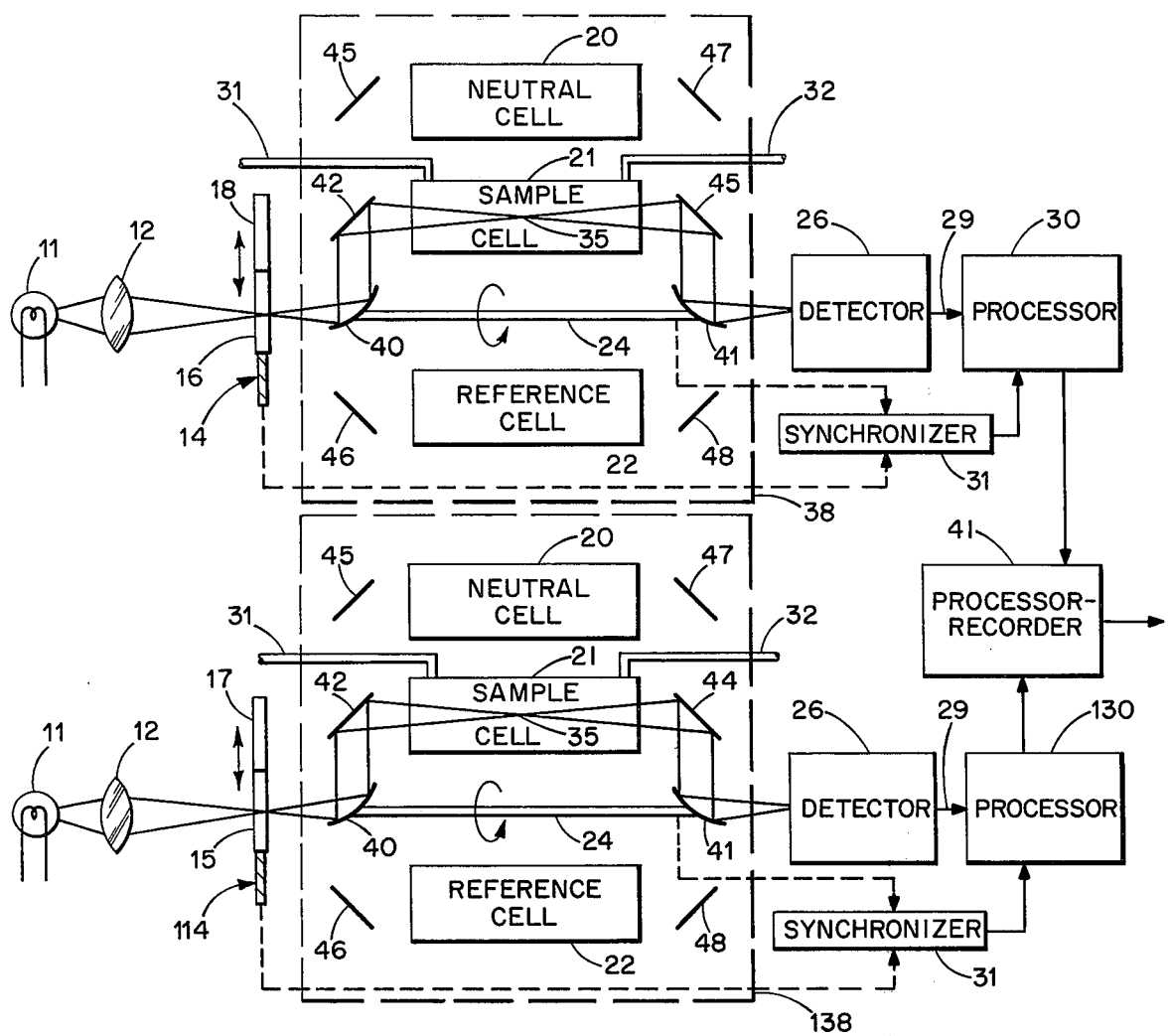
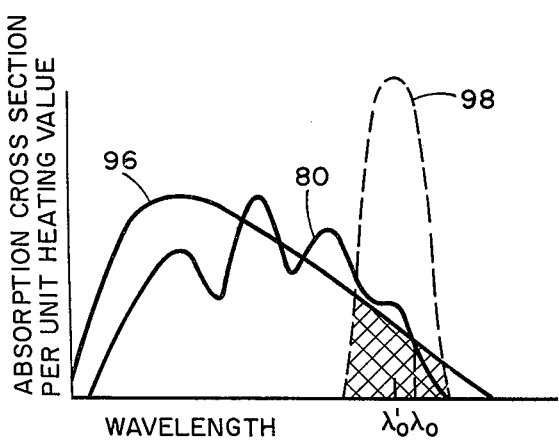
Fig. 10.
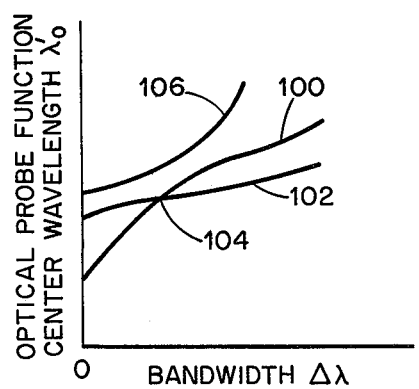
Fig. 11.

MEASURING THE HEATING VALUE OF A FUEL IN THE GASEOUS STATE: METHOD AND APPARATUS

BACKGROUND OF THE INVENTION

This invention relates generally to calorimetry and in particular to a spectrophotometric method of measuring the heating value of a fuel in the gaseous state. The term heating value as hereafter applied means the amount of heat which would be liberated by combustion from a known quantity of a substance. The term total heating value used herein refers to the aggregate of heating values contributed by each of the constituents of a mixture of substances.

The heating value of a substance is of significant interest because it forms one basis for determining the commercial value of that substance as a fuel. The combustible constituents of a typical gaseous fuel such as natural gas or substitute natural gas (SNG) comprise the hydrocarbons methane, ethane, propane, butane, pentane, and their isomers. Collectively these hydrocarbons, known as the saturated or paraffin hydrocarbons, constitute a homologous series in which members differ by the increment $CH_2$. In a typical gaseous fuel mixture, methane, $CH_4$, the simplest constituent, accounts for more than eighty percent (by volume) of the fuel. The heavier paraffin hydrocarbon constituents denoted hereafter as the "ethane-plus" constituents, generally account for the balance of significant combustible components. Before transmission to the distribution mains, typical purification procedures remove undesirable impurities and many of the other hydrocarbons which are present in the unpurified gas. Thus, in determining total heating value, it is often possible to disregard constituents other than the paraffin hydrocarbons.

The conventional methods of measuring heating value known to the art are (1) combustion calorimetry, (2) gas chromatography, and (3) mass spectrometry. Combustion calorimetry is the direct measure of heat liberated by combustion. Gas chromatography and mass spectrometry are techniques of separating and identifying each constituent and measuring the relative concentration thereof. Knowing the heating value of each constituent of a mixture, the total heating value may then be computed. A further method of identifying each constituent and measuring the relative concentration thereof is absorption spectroscopy. However, the absorption spectroscopy method has heretofore found little application to calorimetry because of practical difficulties in accurately measuring the relative concentration of all constituents of interest.

Although all of the aforementioned techniques are of some value in certain applications, each is subject to one or more deficiencies, among which are the following:

1. Operation requiring trained personnel;
2. Delay in obtaining results;
3. Lack of repeatability;
4. Destruction of sample;
5. Cumbersome or expensive instrumentation;
6. Lack of accuracy due to inability to completely distinguish constituents.

SUMMARY OF THE INVENTION

It is the general purpose of this invention to provide a simple and accurate method of measuring the total heating value of a mixture of known gaseous materials. This is accomplished by measuring the strength of radiant absorption of a sample of the mixture illuminated by a radiant energy source having known spectral characteristics. The invention incorporates the recognition that at least one particular waveband exists within which more than one constituent of the mixture exhibit radiant absorption in proportion to their characteristic heating value. It has been found that, in a waveband centered near 6.83 microns, the common paraffin hydrocarbons found in natural gas and SNG, except methane, exhibit radiant absorption in approximately linear proportion to their heating value.

Accordingly, an object of this invention is to provide a novel method for determining the total heating value of a combustible substance in the gaseous state.

Another object is to provide a simple method of calorimetry for gaseous fuels without assaying a sample or expending a portion thereof.

A further object is to provide a calorimeter for the accurate, repeatable and continuous observation of the heating value of gaseous fuels commonly known as natural gas and SNG.

A still further object is to render practicable an instrument adapted for field measurements of the heating value of natural gas, having sufficient accuracy for commercial purposes.

It is a further object of this invention to observe the radiant energy absorption spectrum of a mixture of substances in such a manner as to yield useful information without direct reference to the presence or relative concentration of the individual constituents.

Further objects and features will become apparent upon reference to the following description together with the drawings.

BRIEF DESCRIPTION OF THE DRAWINGS

FIG. 5 is a schematic diagram, partially in block form, of a first embodiment of an apparatus employing the inventive method.

FIG. 10 is an illustration similar to that of FIG. 9 showing the use of the absorption cross-section in measuring the heating value of a third species.

FIG. 11 is a curve of bandwidth versus optical probe function center wavelength.

DETAILED DESCRIPTION OF THE DRAWINGS

Figure 1:
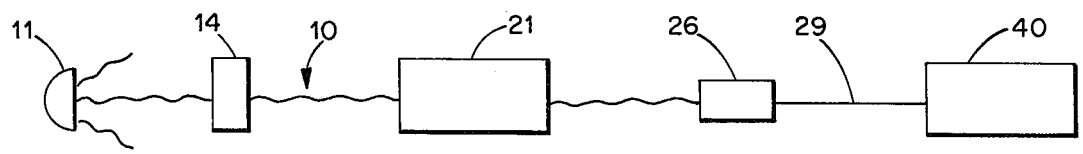
FIG. 1 is a block diagram of an apparatus for performing the method of this invention.

Referring to FIG. 1, an apparatus incorporating the inventive method is depicted, including a radiant energy source 11, waveband selector means 14, an optically transparent cell 21 adapted to contain samples of the substance of which the heating value is to be measured, an optical detector 26 and a multiple function signal processor-recorder 40 connected by electrically conductive means 29 to the detector 26.

Figure 2:
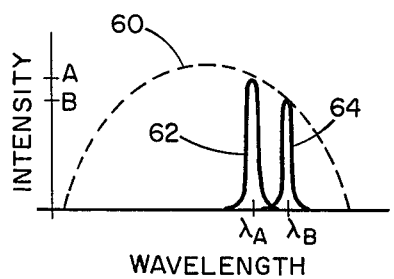
FIG. 2 is a graph of intensity versus wavelength of a typical illuminating source showing a pair of narrow spectral bands selected therefrom.
Figure 3:
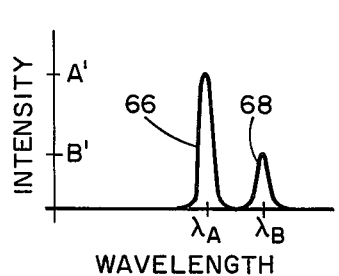
FIG. 3 is a graph of intensity versus wavelength showing the pair of narrow spectral bands selected in FIG. 2 measured through a sample having unknown radiant absorption in one of the narrow spectral bands.

To illustrate one use of the invention in measuring the heating value of a gaseous substance placed in the sample cell 21, reference is made to FIG. 1 through FIG. 3. The radiant energy source 11 and the waveband selector means 14 interact to form a radiant energy probing means 10 for direction through the sample cell 21. The radiant energy probing means 10 has the desired spectral characteristic that radiation therefrom which is passed through the sample and which impinges on the detector 26 will have an intensity correlated with the heating value of the sample.

By way of illustration, the source 11 may be an incandescent filament. Curve 60 of FIG. 2 represents the broad spectral character of the radiation emitted by source 11. Waveband selector means may comprise optical filters of suitable transmission characteristics. Curves 62 and 64 represent the radiation passed by optical filters of suitably narrow wavebands centered at a pair of selected wavelengths $\lambda_A$ and $\lambda_B$.

Figure 4:
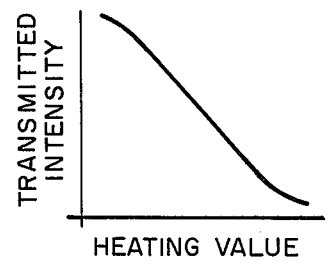
FIG. 4 is a graph representing radiant transmittance versus heating value for a mixture of constituents which exhibit radiant absorption in a narrow waveband centered near 6.83 microns.

The two wavelengths are chosen such that radiation of wavelength $\lambda_A$ is not substantially absorbed by the sample while radiation of wavelength $\lambda_B$ is absorbed by the sample in proportion to aggregate heating value of certain of the constituents of the mixture, as represented by the relation depicted in FIG. 4.

Curves 66 and 68 of FIG. 3 illustrate the intensities A and B' of radiant energy at wavelengths $\lambda_A$ and $\lambda_B$ which have passed through the sample cell 21, wherein the intensity of $\lambda_B$ has been reduced to B' by radiant absorption in the measured sample.

The aggregate heating value of the aforesaid certain constituents is ascertained by comparing the radiant energy intensities at $\lambda_A$ and $\lambda_B$ passed by the sample.

The invention is based on the recognition that in regions where spectra overlap a waveband can be selected which, when the absorption therein is measured, will yield useful information about the constituents having overlapped spectra. By way of example, it has been found that a radiant energy probing means having a characteristic spectrum comprising a narrow waveband which includes a wavelength of 6.83 microns and has a half-power bandwidth of one to two percent yields a transmitted intensity through the mixtures of the "ethane-plus" constituents typical to gaseous fuels which is approximately linearly proportional to the heating value of the "ethane-plus" mixture. Use of a narrow band radiant energy probing means having a characteristic spectrum centered near 6.83 microns and with a half-power bandwidth of 1½% is acceptable for measuring the contribution of the "ethane-plus" constituents to the total heating value of a gaseous fuel.

The heating value of the methane constituent may be ascertained in a similar manner by measuring the amount of radiant energy absorbed in a narrow band selected for its response to the relative concentration of methane. From the intensity value obtained, which corresponds to the relative concentration of methane, the heating value attributable to methane may be computed.

The computation of the total heating value is made according to a function of the nature:

$$H_T = H_M \times C_M + \Theta \times H_E \times C_E$$

where $H_T$ is the total heating value of the fuel;

$H_M$ is the heating value of the methane constituent;

$C_M$ is the fractional relative concentration of the methane constituent;

$H_E$ is the composite heating value per unit of radiant energy absorbed of the constituents which exhibit radiant energy absorption in a narrow waveband centered at 6.83 microns;

$C_E$ is the measured amount of radiant energy absorbed in the aforementioned 6.83 microns waveband; and $\Theta$ is a predetermined compensating factor for improving calibration.

Although the method of the invention suggests a narrow waveband absorption measurement to determine the relative concentration of methane, any other convenient method may be employed which measures the contribution of the methane constituent to the heating value. The heating value of any other significant constituents may be similarly determined.

The inventive method may be carried out using a suitable infra-red absorption instrument adapted to achieve the selectivity and accuracy required for the application. For example, a commercial infra-red dual-beam spectrophotometer adapted to measuring the sample absorption at each pair of wavelengths $\lambda_A$ and $\lambda_B$ referred to above could be employed. A preferred embodiment of an apparatus employing the invention is an improvement on an apparatus of the type disclosed in the co-pending U.S. patent application Ser. No. 353,307, filed Apr. 23, 1973, now U.S. Pat. No. 3,853,407 in the name of the present inventor, C. Forbes Dewey, Jr., entitled "Multiple Path Spectrophotometer Method and Apparatus". Accordingly, reference is made to the co-pending application.

FIG. 5 shows a schematic diagram of an apparatus similar to one disclosed in the co-pending U.S. patent application comprising a first analyzer 38 and a second analyzer 138. In this embodiment the first analyzer is adapted to measure the concentration of methane and thereby determine its heating value and the second analyzer is adapted to measure the heating value of the "ethane-plus" constituents by the method of this invention. Each analyzer includes a light source 11, light collection system 12, first waveband selector means 14 for the methane analyzer 38, second waveband selector means 114 for the ethane-plus analyzer, wherein each waveband selector means comprises at least two filter elements 15, 17; and 16, 18; for selecting in alternation narrow spectral bands from each source 11. One of the filter elements in the second wavelength selector means 114 is adapted to pass radiant energy in a narrow waveband which includes 6.83 microns. The filter elements 15, 17; and 16, 18; cooperate to select wavelengths which correspond to $\lambda_A$ and $\lambda_B$ as aforementioned in the description of the inventive method.

Following each waveband selector means 14 and 114, are a plurality of optically transparent cells, a neutral cell 20, a sample 21, and a reference cell 22, arranged in parallel and the latter two adapted to contain unknown samples and calibration samples as described in the aforementioned co-pending U.S. patent application. Tubing, 31 and 32, connected in series or in parallel communicates unknown samples with each sample cell 21. Each cluster of three cells, 20, 21, and 22, is positioned at equal radial distance from each rotatable shaft 24. Concave mirrors 40 and 41 on each rotatable shaft 24 intercept illumination, focus it and direct in alternation through each sample cell 21, neutral cell 20, and reference cell 22, by the use of mirrors 42, 44, 45, 47; and 46, 48; placed at equal radial distance around each rotatable shaft 24. Fixed position mirrors may be replaced by a set of rotatable mirrors arranged in periscopes at opposing ends of each shaft 24.

Illumination passed through selected cells is directed to respective detectors 26 which converts intensity information to an electrical signal suitable for processing. The detectors 26 are of the type commonly used in optical spectroscopy. If desired, detectors 26 can be placed elsewhere with suitable optics directing the illumination thereto. An electrical connector 29 from each respective detector 26 transmits the signals respectively to a first signal processor 30, associated with the methane analyzer 38, and a second signal processor 130, associated with the "ethane-plus" analyzer 138. A synchronizer 31 with each analyzer 38 and 138 cooperates with each respective wavelength selector 14 and 114 and each respective shaft 24 to indicate to the respective processors 30 and 130 the wavelength being transmitted and the cell being illuminated. Synchronization information may be provided in any usual manner. The methane processor 30 employs intensity information from its detector indicative of the relative concentration of methane to compute the heating value of the methane constituent. The "ethane-plus" processor 130 uses intensity information from its detector to compute the composite heating value of the "ethane-plus" constituents without direct reference to the relative concentration of the individual constituents. A processor-recorder 41 receives information from the respective processors 30 and 130 to determine and record the total heating value of the gaseous fuel.

Although the detectors 26, the synchronizers 31, the processors 30 and 130, and the processor-recorder 41 are shown as separate units, it is obvious that the functions can be incorporated into an integrated unit.

In this embodiment, the filter elements 15, 17; and 16, 18; of the respective wavelength selectors 14 and 114 each comprise a suitable multilayer dielectric filter having a narrow passband. For example, a 1½% passband is acceptable. Any other of the usual wavelength selective means may be used, including additional fixed filters and gas cell filters, which may be placed conveniently in the illumination path between the source 11 and the detector 26. Use of one or more radiation sources of suitable spectral characteristics in place of the black body radiation sources 11 suggests the elimination of filters.

Figure 6:
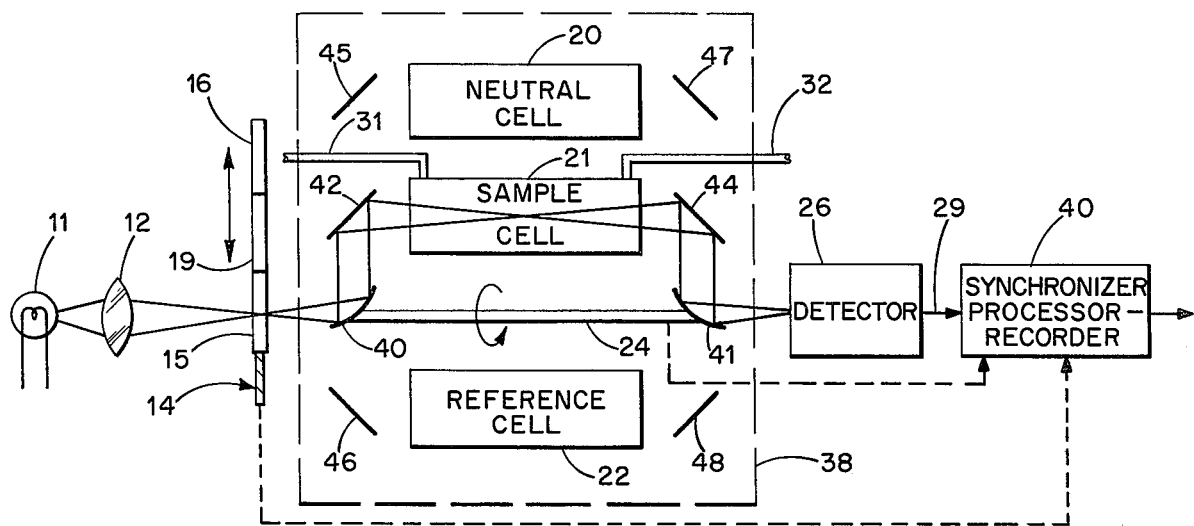
FIG. 6 is a schematic diagram, partially in block form, of a second embodiment of an apparatus employing the inventive method.

FIG. 6 illustrates in block diagram form a further apparatus employing the inventive method to measure the heating value of a gaseous fuel comprising methane and ethane-plus constituents. A single sample cell 21 is employed to make the necessary unknown measurements. The wavelength selector means 14 comprises an optical bandpass filter of the type previously described adapted to pass the wavelength of 6.83 microns, denoted the ethane-plus filter 15, an optical bandpass filter adapted to pass a wavelength selected for its responsivity to the relative concentration of methane, denoted the methane filter 16, and an optical bandpass filter adapted to pass a wavelength selected for its lack of responsivity to the presence of either methane or the ethane-plus constituents. This last-described filter is denoted the neutral reference filter 19. The neutral reference filter 19 provides the function of selecting the wavelength $\lambda_4$ for both the methane measurement and the ethane-plus measurement as set forth in the aforementioned description of the inventive method.

Figure 7:
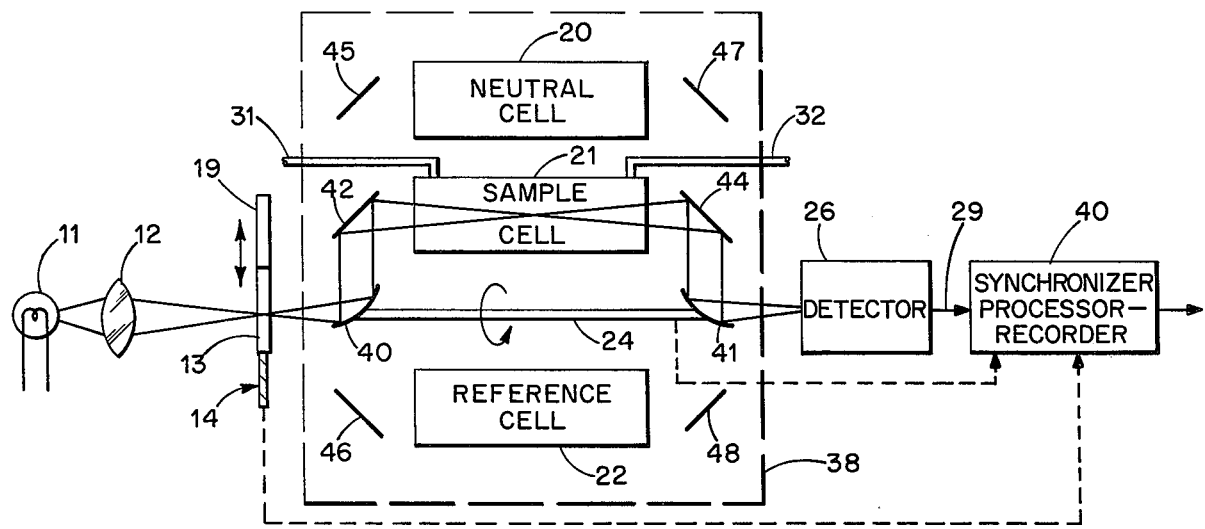
FIG. 7 is a schematic diagram, partially in block form, of another embodiment of the invention.

A still further apparatus employing the inventive method is shown in block diagram form in FIG. 7. The waveband selector means 14 herein comprises a neutral reference filter 19 and a multiple passband filter 13 which combines the functions of the ethane-plus filter 15 and the methane filter 16 such that the processor of the unit 40 interprets intensity information derived from the resultant spectra as corresponding to the total heating value of the sample. In this embodiment it is understood that the relative transmission by the filter 13 within the two measuring wavebands must be adjusted to a specific empirically determined ratio. In this manner the number of measuring steps used to determine the total heating value is further reduced.

While the feasibility of the inventive method has been proven empirically, the following principles will help by way of explanation. It is not intended as limiting of the invention but is presented as the theory of operation. Application of procedures based on the principles will suggest further embodiments of the apparatus employing the inventive method. Reference is made to FIGS. 8 – 11 which accompany the following explanation.

Figure 8:
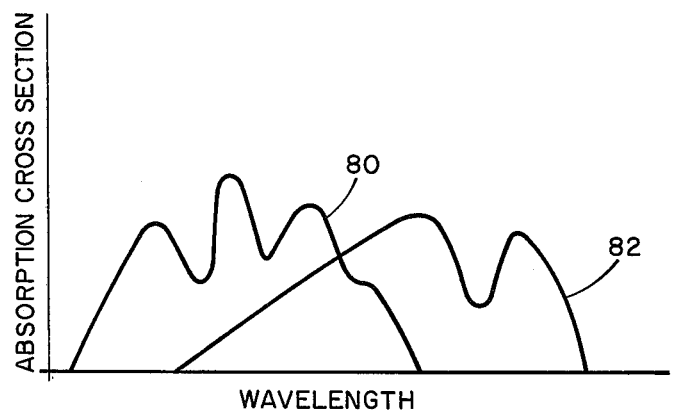
FIG. 8 is a plot of wavelength versus absorption cross-section for two species having overlapping spectra.
Figure 9:
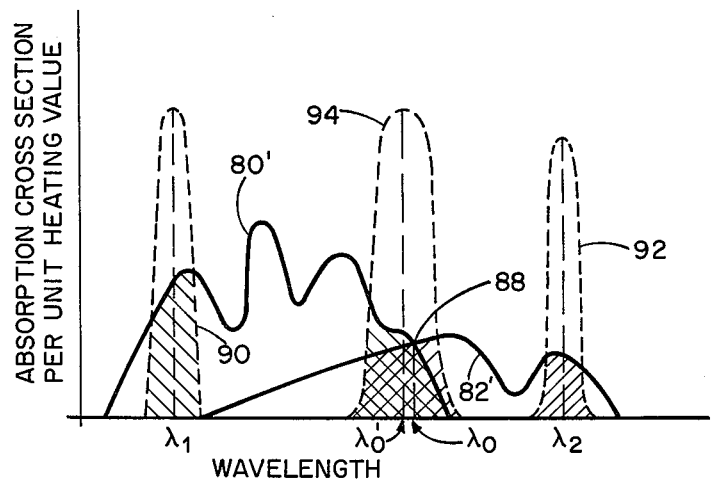
FIG. 9 illustrates the use of the absorption cross-section of FIG. 8 in measuring heating value.

The absorption of radiant energy by chemical species in the gaseous state is a function of temperature, pressure, concentration and thickness of a sample thereof. However, each chemical species exhibits a unique function related to absorption when observed under standardized conditions. The unique absorption function is denoted as the absorption cross-section per molecule. A plot of wavelength versus absorption cross-section for two species having overlapping spectra is depicted in FIG. 8. Curve 80 represents the absorption cross-section of a first species having a heating value of, for example, 100. Curve 82 represents the absorption cross-section of a second species having a heating value of, for example, 50. In FIG. 9, the absorption cross-sections for the species represented by curves 80 and 82 are appropriately normalized and plotted in a graph of wavelength versus absorption cross-section per unit heating value, wherein the curve 80 corresponds to a curve 80' and the curve 82 corresponds to a curve 82'. At a wavelength $\lambda_1$, the absorption of the first species can be measured without interference from the spectra of the second species. Optical measurement methods commonly measure absorption over a band of wavelengths simultaneously, as represented by a curve 90 centered at $\lambda_1$ and designated as an optical probe function $h_1(\lambda)$. Since the heating value is approximately linearly proportional to the absorption over the range of conditions of interest, the heating value of the single species can be determined by a relation of the form $$HV_1 = K_1 \times I_1$$

$$K_1 = C \int_0^\infty h_1(\lambda) f_1(\lambda) \, d\lambda \qquad 5$$

$HV_1$ is the heating value of the first species;
$I_1$ is the fractional absorption of incident radiation within the entire optical probe function $h_1$;
$K_1$ is a constant determined as above;
$h_1(\lambda)$ is an optical probe function centered at $\lambda_1$ represented by the curve 90;
$f_1(\lambda)$ is the absorption cross-section per unit heating value of the first species represented by the curve 80'; and
$C$ is a constant which is independent of $\lambda$ and determined by the optical details of the apparatus employed, including the absorption path length, and is known for a given apparatus.

Modifications of the above equation may be made to account for a nonlinear relationship between heating value and absorption.

Similarly a relation for the second species can be formulated in the form $$HV_2 = K_2 \times I_2$$

$$K_2 = C \int_0^\infty h_2(\lambda) f_2(\lambda) \, d\lambda$$

where
$HV_2$ is the heating value of the first species;
$I_2$ is the fractional absorption of incident radiation within the entire optical probe function $h_2$;
$K_2$ is a constant selected for correlating heating value to absorption at $\lambda_2$ of the second species;
$h_2(\lambda)$ is an optical probe function centered at $\lambda 2$ represented by the curve 92;
$f_2(\lambda)$ is the absorption cross-section per unit heating value of the second species represented by the curve 82'; and
$C$ is the instrumental constant previously described.

At a wavelength $\lambda_o$ the overlapping absorption cross-sections of the first and second species coincide, at a point 88, such that the species have an identical heating value constant $K_o$. Therefore an observation of the absorption of a mixture of the first and second species in an infinitely narrow waveband centered at $\lambda_o$ will be proportional to the heating value of a mixture thereof. However because optical detection methods normally measure intensity over a band of wavelengths, $\Delta\lambda_o$, the optical probe function, which produces an identical heating value constant $K_o$, is offset to a wavelength centered at $\lambda_o'$. The desired optical probe function $h_o'(\lambda)$ is represented by a curve 94. The heating value of the mixture is determined by a relation of the form $$HV = K_o \times I$$

$$2 K_o = C \int_0^\infty [f_1(\lambda) + f_2(\lambda)] h_o(\lambda) \, d\lambda$$

where $I$ is the measured fractional absorption of incident radiation within the entire optical probe function $h_o$;
$f_1(\lambda)$ is the absorption cross-section per unit heating value of the first species as represented by curve 80';
$f_2(\lambda)$ is the absorption cross-section per unit heating value of the second species as represented for example by the curve 82';
$K_o$ is the heating value constant common to each species;
$h_o'(\lambda)$ is an optical probe function centered at $\lambda_o'$; and
$C$ is the instrumental constant previously described.

It is apparent from an examination of FIG. 9 that the value of $\lambda_o'$, at which the heating value constant ($K_1$) of the first species will equal the heating value constant ($K_2$) of the second species, varies as the width of the waveband $\Delta\lambda_o$ is increased or decreased. Thus, in general, one may plot a curve of $\lambda_o'$ versus $\Delta\lambda_o$ which represents possible solutions to the equation $$K_1 = K_2 = K_o,$$

where $K_o$ is a common heating value constant. This curve is represented in FIG. 11 as curve 100.

FIG. 10 shows a plot of wavelength versus absorption cross-section per unit heating value for the first species as represented by the curve 80' and a third species as represented by the curve 96. The third species has a characteristic spectra which overlaps both the first species and the second species. An optical probe function $h_o(\lambda)$ represented by the curve 98 has a center wavelength $\lambda_o'$ and bandwidth $\Delta\lambda_o$ such that the first and third species have an identical heating constant $K_o$.

As demonstrated above, the center wavelengths $\lambda_o'$ at which the common heating value constant $K_o$ ($K_o = K_1 = K_3$) may occur vary according to the bandwidth $\Delta\lambda_o$ of the optical probe function $h_o(\lambda)$. In FIG. 11, curve 100 is a plot of bandwidth versus optical probe function center wavelength $\lambda_o'$ for the common heating value constant K of the first and second species. Curve 102 is a similar plot for the first and third species. Because the species have overlapping spectra, the common heating value plots may intersect. If the common heating value plots intersect, as illustrated at point 104 of FIG. 11, a combination of the parameters $\lambda_o'$ and $\Delta\lambda_o$ exists which can be used to exactly correlate the heating value of the mixture of the three species with the intensity of absorption within the region specified by the optical probe function $h_o(\lambda)$. When the exact correlation exists between two or more overlapping spectra, the value $\Theta$ in the function for computing total heating value, discussed above, is unity.

Overlapping spectra of further species may occur which have a common heating value constant characteristics which are close to the common heating value constant characteristics of the other species. Such a characteristic is represented by the curve 106. Within the range of relative concentrations which may be encountered in practice, the common heating value characteristics of all species may be sufficiently close that a single absorption measurement may yield the total heating value of the mixture to an acceptable accuracy. In these situations, the value $\Theta$ in the function for computing total heating value may be empirically adjusted (typically to a value between 0.8 and 1.3) to improve the level of accuracy.

Based on the foregoing description of the determination of heating value, it appears that gaseous substances can be observed in such a manner to produce similar characteristic correlations between radiant absorption and other information of interest.

The invention herein described demonstrates that the radiant energy absorption spectrum of a mixture of substances can be observed in such a manner as to yield useful information without direct reference to the presence or relative concentration of the individual constituents.

It is recognized that the sensitivity of an embodiment employing this inventive method is limited according to the difficulty of measuring radiant absorption over a wide range of concentrations and mixtures. Because of this limitation, it is advisable to employ the inventive method together with an apparatus having dynamic range, compensation, and calibration capabilities appropriate to the application thereof. Such capabilities may include interchangeablity of cells of various lengths, means for measuring additional significant constituents either individually or in aggregate, and appropriate scaling functions as part of a signal processing means.

While the present invention has been described in reference to various embodiments thereof, many changes and variations will be apparent to those skilled in the art, and such can obviously be made without departing from the scope of the invention.

What is claimed is:

1. A method of measuring the heating value of a fuel in the gaseous state and having two or more constituents with overlapping spectra in at least one region, said method comprising the steps of:
   a. measuring the amount of radiant energy absorbed by such fuel in a spectral region where two or more constituents have overlapping spectra and energy absorption is a known function of the composite contribution to said heating value by the constituents having overlapping spectra in said spectral region;
   b. measuring the relative concentration of other constituents which contribute to the heating value of such fuel, the concentration of each of said other constituents being proportional to its heating value contribution, thereby to obtain the heating value contribution of the other constituents; and
   c. combining heating value contributions from said measuring steps.

2. A method according to claim 1 wherein the relative concentration of said other contributing constituents is measured by observing the amount of radiant energy absorbed in a second spectral region.

3. A method according to claim 1 wherein the spectral characteristics of said first spectral region comprise passband having a half-power bandwidth of approximately 1.5% centered at a wavelength of approximately 6.83 microns.

4. A method according to claim 2 wherein the measurements in said first spectral region and said second spectral region are performed concurrently.

5. A method according to claim 2 wherein the measurements in said first spectral region and said second spectral region are performed alternately in rapid sequence.

6. A method of measuring the heating value of paraffin hydrocarbon constituents in a fuel in the gaseous state comprising the steps of:
   a. measuring the amount of radiant energy absorbed in a narrow waveband centered at approximately 6.83 microns to obtain information indicative of the composite contribution to the heating value by the paraffin hydrocarbon constituents of the fuel other than methane, said absorbed energy being a known function of said composite contribution to the heating value;
   b. measuring the amount of radiant energy absorbed at a predetermined wavelength to obtain information indicative of the relative concentration of the methane constituent in said fuel, said concentration being proportional to the heating value contribution of the methane constituent, thereby to obtain information indicative of the contribution to heating value of the methane constituent;
   c. obtaining information for the purpose of calibration by measuring the amount of radiant energy absorbed by known quantities of known materials in the gaseous state at said wavelengths; and
   d. combining information indicative of heating value contributions for obtaining a measurement of heating value.

7. A method according to claim 6, wherein said measuring method is continuous.

8. A method of measuring the heating value contribution of two or more specific species within a gaseous mixture comprising the steps of irradiating the gaseous mixture with radiant energy in a waveband centered approximately in a spectral region such that $$\int_0^\infty h(\lambda) f(\lambda) \, d\lambda$$

is approximately equal for all such specific species, where
- $h(\lambda)$ = the optical probe function centered at waveband $\lambda$ and
- $f(\lambda)$ is the absorption cross-section per unit heating value of a selected species, and measuring the amount of said radiant energy absorbed by the gaseous mixture.

9. The method of claim 8 wherein said waveband is characterized by a half-power bandwidth of approximately 1.5%.

10. A method of measuring, within a gaseous mixture, the heating value contribution of two or more paraffin hydrocarbons which have two or more carbon atoms comprising the steps of irradiating the gaseous fuel with radiant energy in a waveband centered at approximately 6.83 microns, whereby the absorbed radiant energy is a known function of the heating value of said paraffin hydrocarbons, and measuring the amount of said radiant energy absorbed by the gaseous mixture.

11. A method according to claim 10 wherein said waveband is characterized by a half-power bandwidth of approximately 1.5%.

* * * * *